United States Patent [19]

Cotrel et al.

[11] 4,131,674
[45] Dec. 26, 1978

[54] NAPHTYRIDINE DERIVATIVES

[75] Inventors: Claude Cotrel, Paris; Cornel Crisan, Sceaux; Claude Jeanmart, Brunoy; André Léger, Paris, all of France

[73] Assignee: Rhone-Poulenc Industries, Paris, France

[21] Appl. No.: 843,369

[22] Filed: Oct. 19, 1977

Related U.S. Application Data

[62] Division of Ser. No. 673,868, Apr. 5, 1976.

[30] Foreign Application Priority Data

Apr. 7, 1975 [FR] France .................. 75 10756
Feb. 11, 1976 [FR] France .................. 76 03773
Feb. 11, 1976 [FR] France .................. 76 03774

[51] Int. Cl.² .............. C07D 471/04; A61K 31/535
[52] U.S. Cl. .............................. 424/248.54; 544/127
[58] Field of Search .................. 544/127; 424/248.54

[56] References Cited
PUBLICATIONS

Cotrel et al., "Chem. Abstracts," vol. 85, (1976), No. 46758m.

*Primary Examiner*—Natalie Trousof
*Assistant Examiner*—R. W. Ramsuer
*Attorney, Agent, or Firm*—Stevens, Davis, Miller & Mosher

[57] ABSTRACT

Heterocyclic compounds of the formula:

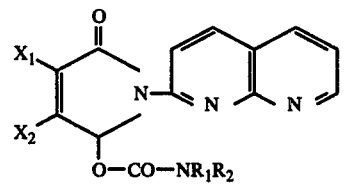

wherein the pyrroline ring and the symbols $X_1$ and $X_2$ together form an unsubstituted or substituted isoindoline nucleus, or a 6,7-dihydro-5H-pyrrolo[3,4-b]pyrazine, 6,7-dihydro-5H-pyrrolo[3,4-b]pyridine or 2,3,6,7-tetrahydro-5H-1,4-oxathiino[2,3-c]pyrrole nucleus, the 1,8-naphthyridin-2-yl nucleus is unsubstituted or substituted, and the grouping $-NR_1R_2$ is an amino or substituted amino group, are new compounds which are active as tranquillizers, hypnotics, anti-convulsant agents and anti-spasmodics.

6 Claims, No Drawings

NAPHTYRIDINE DERIVATIVES

This is a division of application Ser. No. 673,868 filed April 5, 1976.

This invention relates to new therapeutically useful heterocyclic compounds, to processes for their preparation and pharmaceutical compositions containing them.

The new heterocyclic compounds of the present invention are those of the general formula:

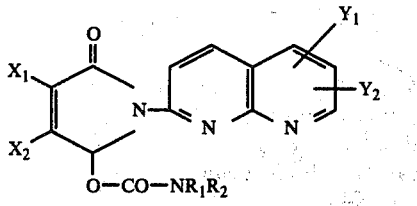

wherein the pyrroline ring and the symbols $X_1$ and $X_2$ together form an isoindoline nucleus (optionally substituted by one or two atoms or radicals which — when two substituents are present — may be the same or different selected from halogen atoms (preferably chlorine), alkyl radicals containing 1 to 4 carbon atoms, alkoxy radicals containing 1 to 4 carbon atoms, and the nitro and trifluoromethyl radicals), or a 6,7-dihydro-5H-pyrrolo[3,4-b]pyrazine, 6,7-dihydro-5H-pyrrolo[3,4-b]pyridine or 2,3,6,7-tetrahydro-5H-1,4-oxathiino[2,3-c]pyrrole nucleus, the symbols $Y_1$ and $Y_2$ are the same or different and each represents a hydrogen or halogen atom (preferably chlorine), or an alkyl radical containing 1 to 4 carbon atoms, an alkoxy radical containing 1 to 4 carbon atoms, or the cyano radical, and the symbols $R_1$ and $R_2$ are the same or different and each represent a hydrogen atom or an alkyl radical containing 1 to 12 carbon atoms (which is optionally substituted by a hydroxy radical, an alkoxy radical containing 1 to 4 carbon atoms, a phenyl radical, an amino radical, a monoalkylamino group of which the alkyl radical contains 1 to 4 carbon atoms, a dialkylamino group of which each alkyl radical contains 1 to 4 carbon atoms or the alkyl radicals together with the nitrogen atom to which they are attached form a saturated five- or six-membered heterocyclic ring, or an alkoxycarbonyl group of which the alkoxy radical contains 1 to 4 carbon atoms), an alkenyl radical containing 3 or 4 carbon atoms, an alkynyl radical containing 3 or 4 carbon atoms, or a cycloalkyl radical containing 3 to 6 carbon atoms, or $R_1$ and $R_2$ together with the nitrogen atom to which they are attached form a saturated five- or six-membered heterocyclic ring which optionally contains a second hetero atom selected from oxygen and sulphur, e.g. piperidino or morpholino, and when appropriate — as hereinafter mentioned — acid addition salts thereof.

According to a feature of the invention, the compounds of general formula I, wherein $X_1$, $X_2$, $Y_1$, $Y_2$, $R_1$ and $R_2$ are as hereinbefore defined, are prepared by the process which comprises reacting an amine of the general formula:

$$HNR_1R_2 \qquad II$$

(wherein $R_1$ and $R_2$ are as hereinbefore defined) with a mixed carbonate of the general formula:

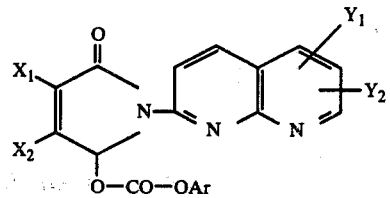

wherein $X_1$, $X_2$, $Y_1$ and $Y_2$ are as hereinbefore defined and Ar represents a phenyl radical optionally substituted by an alkyl radical containing 1 to 4 carbon atoms or the nitro radical. The reaction is generally carried out in an anhydrous organic solvent e.g. acetonitrile or dimethylformamide, at a temperature between 20° and 100° C.

The mixed carbonates of general formula III can be obtained by reaction of a chloroformate of the general formula:

$$Cl-CO-O-Ar \qquad IV$$

(wherein Ar is as hereinbefore defined) with a compound of the general formula:

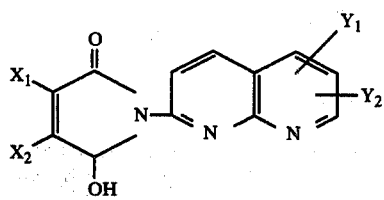

wherein $X_1$, $X_2$, $Y_1$ and $Y_2$ are as hereinbefore defined. The reaction is generally carried out in a basic organic solvent such as pyridine and preferably at a temperature between 0° and 60° C.

The compounds of general formula V can be obtained by partial reduction of an imide of the general formula:

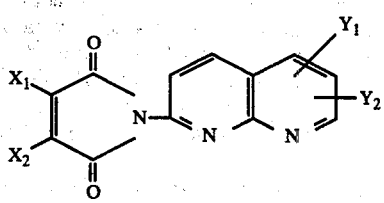

wherein the various symbols are as hereinbefore defined. The reduction is generally effected by means of an alkali metal borohydride in an organic or aqueous-organic solution, for example in a mixture of dioxan and water, dioxan and methanol, methanol and water, ethanol and water or tetrahydrofuran and methanol.

The partial reduction of a compound of general formula VI in which the pyrroline ring and the symbols $X_1$ and $X_2$ together form an isoindoline nucleus which is substituted as indicated above, or a 6,7-dihydro-5H-pyrrolo[3,4-b]pyridine or 2,3,6,7-tetrahydro-5H-1,4-oxathiino[2,3-c]pyrrole nucleus, can give isomeric products which can be separated by physico-chemical methods such as fractional crystallisation or chromatography.

The imides of general formula VI can be obtained by reaction of a 2-aminonaphthyridine of the general formula:

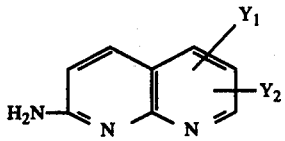

VII (wherein $Y_1$ and $Y_2$ are as hereinbefore defined) with an anhydride of the general formula:

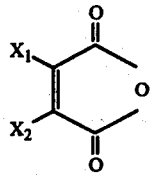

VIII (wherein $X_1$ and $X_2$ are as hereinbefore defined), the imide product being obtained via an intermediate compound of the general formula:

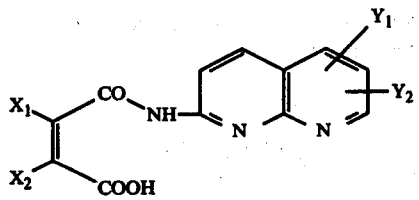

IX wherein the various symbols are as hereinbefore defined. The reaction of the 2-aminonaphthyridine of general formula VII with the anhydride of general formula VIII is carried out by heating in an organic solvent, e.g. ethanol, acetic acid, dimethylformamide, acetonitrile or diphenyl ether, or in dimethylformamide in the presence of N,N'-dicyclohexylcarbodiimide and N-hydroxysuccinimide.

The cyclisation of the intermediate compound of general formula IX to an imide of general formula VI can be carried out either by heating with acetyl chloride in acetic acid or acetic anhydride, or by the action of a condensing agent such as N,N'-dicyclohexylcarbodiimide in dimethylformamide at a temperature between 20° and 100° C., or by the action of thionyl chloride or phosphorus oxychloride optionally in solution in an organic solvent such as methylene chloride or chloroform.

With reference to general formula VIII, the anhydride of pyrazine-2,3-dicarboxylic acid can be prepared in accordance with the method described by S. Gabriel and A. Sonn, Chem. Ber., 40, 4850 (1907), the anhydride of pyridine-2,3-dicarboxylic acid can be prepared in accordance with the method described by F. F. Blicke and E. L. Jenner, J. Amer. Chem. Soc., 64, 1741 (1942), and the anhydride of 5,6-dihydro-1,4-oxathiine-2,3-dicarboxylic acid can be prepared in accordance with the method of P. ten Haken, J. Het. Chem., 7, 1211 (1970).

The compounds of general formula V, in which the pyrroline ring and the symbols $X_1$ and $X_2$ together form an isoindoline nucleus which is substituted as hereinbefore indicated, can also be prepared in accordance with one of the following methods:

(a) when the isoindoline nucleus is substituted by a halogen atom or an alkoxy radical containing 1 to 4 carbon atoms or a nitro radical, by reaction of a 2-aminonaphthyridine of general formula VII with a halide of o-toluic acid substituted by a halogen atom or an alkoxy radical containing 1 to 4 carbon atoms or the nitro radical, to obtain a product of the general formula:

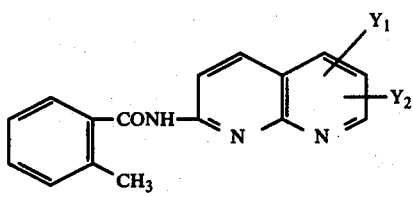

X (wherein $Y_1$ and $Y_2$ are as hereinbefore defined, and the phenyl nucleus is substituted by a halogen atom, an alkoxy radical containing 1 to 4 carbon atoms, or the nitro radical), which compound is then cyclised either by means of N-bromosuccinimide in the presence of azodiisobutyronitrile or via a geminal diester in an aqueous-organic medium, or via a dichloromethyl derivative;

(b) when the isoindoline nucleus is substituted by a nitro radical, by nitration of a compound of general formula V in which the phenyl nucleus is unsubstituted; and (c) when the isoindoline nucleus is substituted by a halogen atom, by replacement of the nitro radical of a compound of general formula V by a halogen atom, via a diazonium salt.

According to a further feature of the invention, the compounds of general formula I wherein $X_1$, $X_2$, $Y_1$ and $Y_2$ are as hereinbefore defined and the symbols $R_1$ and $R_2$ are the same or different and each represents an alkyl radical containing 1 to 12 carbon atoms, an alkenyl radical containing 3 or 4 carbon atoms, an alkynyl radical containing 3 or 4 carbon atoms, or a cycloalkyl radical containing 3 to 6 carbon atoms, or $R_1$ and $R_2$ together with the nitrogen atom to which they are attached form a saturated five- or six-membered heterocyclic ring which optionally contains a second heteroatom selected from oxygen and sulphur, are prepared by the process which comprises reacting a carbamoyl chloride of the general formula:

$$Cl—CO—NR_1R_2$$  XI (wherein $R_1$ and $R_2$ have the meanings just mentioned above) with a compound of general formula V.

Generally, the carbamoyl chloride of general formula XI is reacted with an alkali metal salt, optionally prepared in situ, of a compound of general formula V, the reaction being carried out in an anhydrous organic solvent e.g. dimethylformamide or tetrahydrofuran, at a temperature below 60° C.

The reaction can also be carried out by reacting the carbamoyl chloride of general formula XI with a compound of general formula V, the reaction being carried out in pyridine and optionally in the presence of a tertiary amine such as triethylamine.

According to another feature of the invention, the compounds of general formula I wherein $X_1$, $X_2$, $Y_1$ and $Y_2$ are as hereinbefore defined, $R_1$ represents an alkyl radical containing 1 to 12 carbon atoms (optionally substituted by an alkoxy radical containing 1 to 4 carbon atoms, a phenyl radical or an alkoxycarbonyl group in which the alkoxy radical contains 1 to 4 carbon atoms), an alkenyl radical containing 3 or 4 carbon atoms, an alkynyl radical containing 3 or 4 carbon atoms, or a cycloalkyl radical containing 3 to 6 carbon atoms, and R₂ represents a hydrogen atom, are prepared by the process which comprises reacting an isocyanate of the general formula:

$$O=C=N-R_1',\qquad XII$$

[wherein R₁', represents an alkyl radical containing 1 to 12 carbon atoms (optionally substituted by an alkoxy radical containing 1 to 4 carbon atoms, a phenyl radical or an alkoxycarbonyl group of which the alkoxy radical contains 1 to 4 carbon atoms), an alkenyl radical containing 3 or 4 carbon atoms, an alkynyl radical containing 3 or 4 carbon atoms or a cycloalkyl radical containing 3 to 6 carbon atoms] with a compound of general formula V.

Generally the reaction is carried out in an organic solvent, e.g. acetonitrile, at a temperature between 20° and 100° C. and optionally in the presence of a tertiary amine such as triethylamine.

The heterocyclic compounds of general formula I obtained by the aforedescribed processes can be purified by physical methods such as crystallisation or chromatography, or by chemical methods such as the formation of salts, crystallisation of the salts and decomposition of them in an alkaline medium.

The heterocyclic compounds of general formula I, wherein either or both of symbols R₁ and R₂ represent an alkyl radical substituted by an amino radical, a monoalkylamino group or a dialkylamino group, the alkyl radicals of which may optionally be linked together and with the nitrogen atom form a saturated five- or six-membered heterocyclic ring, can be converted by methods known per se into acid addition salts, for example by reaction of the basic compounds with acids in appropriate solvents, for example alcohols, ethers, ketones or chlorinated hydrocarbons.

The new heterocyclic compounds of general formula I and — when appropriate — their acid addition salts possess useful pharmacological properties; they are particularly active as tranquillisers, hypnotics, anti-convulsant agents and anti-spasmodics.

In animals (mice) they have proved particularly active as such at doses of between 0.1 and 10 mg./kg. animal body weight when administered orally, in particular in the following tests:

(i) electric battle test according to a technique similar to that of Tedeschi et al., J. Pharmacol., 125, 28 (1959), (ii) pentetrazole-induced convulsions according to a technique similar to that of Everett and Richards, J. Pharmacol., 81, 402 (1944).

(iii) supramaximal electro-shock according to the technique of Swinyard et al., J. Pharmacol., 106, 319 (1952), (iv) strychnine mortality according to a technique similar to that of F. Barzaghi et al., Arzneimittelforschung, 23, 683 (1973), and (v) locomotor activity according to the technique of Courvoisier (Congrès des Médecins Aliénistes et Neurologistes, Tours, 8–13th June 1959) and Jolou (Bulletin de la Société de Pharmacie de Lille, No. 2, January 1967, page 7).

Furthermore, they exhibit only a low toxicity; their 50% lethal dose (LD₅₀) in the case of mice is generally greater than 300 mg./kg. animal body weight when administered orally.

Compounds of general formula I of particular value are those in which the pyrroline ring and the symbols X₁ and X₂ together form an isoindoline nucleus (optionally substituted by a halogen atom or a trifluoromethyl radical), a 6,7-dihydro-5H-pyrrolo[3,4-b]pyrazine nucleus or a 6,7-dihydro-5H-pyrrolo[3,4-b]pyridine nucleus, Y₁ represents a halogen atom (preferably chlorine) in the 7-position, Y₂ represents a hydrogen atom, R₁ represents an alkyl radical containing 1 to 6 carbon atoms (optionally substituted by a phenyl radical, an alkoxy radical containing 1 to 4 carbon atoms, a dialkylamino group of which each alkyl radical contains 1 to 4 carbon atoms, or an alkoxycarbonyl group of which the alkoxy radical contains 1 to 4 carbon atoms), an alkenyl radical containing 3 or 4 carbon atoms, e.g. allyl, or a cycloalkyl radical containing 3 to 6 carbon atoms, and R₂ represents a hydrogen atom or an alkyl radical containing 1 to 4 carbon atoms, or R₁ and R₂ together with the nitrogen atom to which they are attached form a saturated five- or six-membered heterocyclic ring which optionally contains an oxygen atom, e.g. piperidino or morpholino.

Compounds of general formula I of more especial value are those in which the pyrroline ring and the symbols X₁ and X₂ form an isoindoline nucleus, Y₁ represents a chlorine atom in the 7-position, Y₂ represents a hydrogen atom, R₁ represents an alkyl radical containing 1 to 6 carbon atoms (optionally substituted by a phenyl radical), an alkenyl radical containing 3 or 4 carbon atoms or a cycloalkyl radical containing 3 to 6 carbon atoms, R₂ represents a hydrogen atom or an alkyl radical containing 1 to 4 carbon atoms, or R₁ and R₂ together with the nitrogen atom to which they are attached form a saturated five- or six-membered heterocyclic ring which optionally contains an oxygen atom.

Amongst the preferred class of compounds there may be mentioned particularly 2-(7-chloro-1,8-naphthyridin-2-yl)-3-methylaminocarbonyloxy-isoindolin-1-one, 2-(7-chloro-1,8-naphthyridin-2-yl)-3-n-butylaminocarbonyloxyisoindolin-1-one, 2-(7-chloro-1,8-naphthyridin-2-yl)-3-piperidinocarbonyloxy-isoindolin-1-one, 2-(7-chloro-1,8-naphthyridin-2-yl)-3-ethylaminocarbonyloxy-isoindolin-1-one, 2-(7-chloro-1,8-naphthyridin-2-yl)-3-propylaminocarbonyloxy-isoindolin-1-one, 2-(7-chloro-1,8-naphthyridin-2-yl)-3-sec-butylaminocarbonyloxy-isoindolin-1-one, 2-(7-chloro-1,8-naphthyridin-2-yl)-3-pentylaminocarbonyloxyisoindolin-1-one, 2-(7-chloro-1,8-naphthyridin-2-yl)-3-cyclopropylaminocarbonyloxy-isoindolin-1-one, 2-(7-chloro-1,8-naphthyridin-2-yl)-3-cyclohexylaminocarbonyloxyisoindolin-1-one, 2-(7-chloro-1,8-naphthyridin-2-yl)-3-cyclopentylaminocarbonyloxy-isoindolin-1-one, 2-(7-chloro-1,8-naphthyridin-2-yl)-3-allylaminocarbonyloxy-isoindolin-1-one, 2-(7-chloro-1,8-naphthyridin-2-yl)-3-n-hexylaminocarbonyloxy-isoindolin-1-one, 2-(7-chloro-1,8-naphthyridin-2-yl)-3-dimethylaminocarbonyloxy-isoindolin-1-one, 2-(7-chloro-1,8-naphthyridin-2-yl)-3-isobutylaminocarbonyloxyisoindolin-1-one, 2-(7-chloro-1,8-naphthyridin-2-yl)-3-benzylaminocarbonyloxy-isoindolin-1-one, 2-(7-chloro-1,8-naphthyridin-2-yl)-3-[(4-morpholino)carbonyloxy]-isoindolin-1-one, 2-(7-chloro-1,8-naphthyridin-2-yl)-3-diethylaminocarbonyloxy-isoindolin-1-one, 2-(7-chloro-1,8-naphthyridin-2-yl)-3-(N-methyl-N-ethylaminocarbonyloxy)-isoindolin-1-one, 2-(7-chloro-1,8-naphthyridin-2-yl)-3-(N-methyl-N-propylaminocarbonyloxy)-isoindolin-1-one, 2-(7-chloro-1,8-naphthyridin-2-yl)-3-(N-butyl-N-methylamino-carbonyloxy)-isoindolin-1-one, 2-(7-chloro-1,8-naphthyridin-2-yl)-3-N,N- dibutylaminocarbonyloxy-isoindolin-1-one and 2-(7-chloro-1,8-naphthyridin-2-yl)-3-(N-methyl-N-pentylaminocarbonyloxy)-isoindolin-1-one.

For therapeutic purposes the heterocyclic compounds of general formula I may be employed as such or — when appropriate — in the form of non-toxic acid addition salts, i.e. salts containing anions which are relatively innocuous to the animal organism in therapeutic doses of the salts (such as hydrochlorides, sulphates, nitrates, phosphates, acetates, propionates, succinates, benzoates, fumarates, maleates, tartrates, theophyllineacetates, salicylates, phenolphthalinates and methylene-bis-$\beta$-hydroxynaphthoates) so that the beneficial physiological properties inherent in the bases are not vitiated by side-effects ascribable to the anions.

The following non-limitative Examples illustrate the invention.

EXAMPLE 1

A 40% (w/v) aqueous solution of methylamine (4.4 cc.) is added, at a temperature of about 20° C., to a suspension of 2-(7-chloro-1,8-naphthyridin-2-yl)-3-phenoxycarbonyloxy-isoindolin-1-one (8.62 g.) in acetonitrile (200 cc.). After 2 hours, the precipitate formed is filtered off and washed with acetonitrile (60 cc.) and then with diethyl ether (60 cc.). A product (7.65 g.) is obtained and is recrystallised from dimethylformamide (140 cc.). 2-(7-Chloro-1,8-naphthyridin-2-yl)-3-methylaminocarbonyloxy-isoindolin-1-one (6.15 g.), melting at 260° C., is thus obtained.

The 2-(7-chloro-1,8-naphthyridin-2-yl)-3-phenoxycarbonyloxy-isoindolin-1-one starting material can be prepared as follows:

Phenyl chloroformate (126 g.) is added to a suspension of 2-(7-chloro-1,8-naphthyridin-2-yl)-3-hydroxyisoindolin-1-one (86.5 g.) in pyridine (980 cc.), whilst keeping the temperature at about 25° C. The reaction mixture is stirred for 3 hours at a temperature of about 20° C., after which it is poured into ice-water (9,000 cc.). The product which crystallises is filtered off, washed with water (6 × 500 cc.) and then with acetonitrile (3 × 200 cc.). After drying, 2-(7-chloro-1,8-naphthyridin-2-yl)-3-phenoxycarbonyloxy-isoindolin-1-one (96.7 g.), melting at 235° C. with decomposition, is obtained.

2-(7-Chloro-1,8-naphthyridin-2-yl)-3-hydroxyisoindolin-1-one can be prepared by adding potassium borohydride (1.72 g.) to a suspension of 2-(7-chloro-1,8-naphthyridin-2-yl)-phthalimide (17.7 g.) in dioxan (87 cc.) and a saturated aqueous solution of disodium phosphate (26.4 cc.), whilst cooling externally with an ice bath. After stirring for 14 hours, the mixture is allowed to return to a temperature of about 20° C. and is stirred for a further 2 hours, and a saturated aqueous solution of disodium phosphate (400 cc.) is then added. The precipitate formed is filtered off and washed with cold water (225 cc.). After drying in air, 2-(7-chloro-1,8-naphythyridin-2-yl)3-hydroxy-isoindolin-1-one (17.5 g.), melting at 248° C., is obtained.

2-(7-Chloro-1,8-naphthyridin-2-yl)-phthalimide can be prepared by heating, at the reflux temperature, a mixture of 2-(7-hydroxy-1,8-naphthyridin-2-yl)-phthalimide (26.3 g.) with phosphorus oxychloride (79 cc.) and dimethylformamide (3.5 cc.) until the evolution of gas ceases. After cooling, the reaction mixture is poured onto ice-water (650 cc.) without allowing the temperature to exceed 25° C. The product obtained is filtered off, washed with water (150 cc.) and dried to constant weight. This gives 2-(7-chloro-1,8-naphthyridin-2-yl)-phthalimide (24.1 g.) melting at 268° C.

2-(7-Hydroxy-1,8-naphthyridin-2-yl)phthalimide can be prepared by heating a mixture of 2-amino-7-hydroxy-1,8-naphthyridine (25 g.) and phthalic anhydride (70 g.) in acetic acid (1,400 cc.) at the reflux temperature for 3 hours. After cooling, the insoluble matter is separated by filtration. The crystals obtained are filtered off and washed successively with diethyl ether (60 cc.), water (90 cc.), a saturated aqueous sodium bicarbonate solution (120 cc.) and finally water (60 cc.). They are then dried to constant weight to give 2-(7-hydroxy-1,8-naphthyridin-2-yl)-phthalimide (17 g.) melting at 370° C.

2-Amino-7-hydroxy-1,8-naphthyridine can be prepared in accordance with the method described by S. Carboni et al., Gazz. Chim. Ital., 95, 1498 (1965).

EXAMPLE 2

Following the procedure of Example 1 but starting with 2-(7-chloro-1,8-naphthyridin-2-yl)-3-phenoxycarbonyloxy-isoindolin-1-one (12.93 g.) and n-butylamine (8.7 cc.) in acetonitrile (300 cc.), 2-(7-chloro-1,8-naphthyridin-2-yl)-3-n-butylaminocarbonyloxy-isoindolin-1-one (8.7 g.), melting at 152° C., is obtained.

EXAMPLE 3

Following the procedure of Example 1 but starting with 2-(7-chloro-1,8-naphthyridin-2-yl)-3-phenoxycarbonyloxy-isoindolin-1-one (8.62 g.) and piperidine (6 cc.) in acetonitrile (200 cc.), 2-(7-chloro-1,8-naphthyridin-2-yl)-3-piperidinocarbonyloxy-1-one (6.5 g.), melting at 223° C., is obtained.

EXAMPLE 4

Following the procedure of Example 1 but starting with 2-(7-chloro-1,8-naphthyridin-2-yl)-3-phenoxycarbonyloxy-isoindolin-1-one (17.24 g.) and 2-diethylaminoethylamine (6.24 cc.) in acetonitrile (400 cc.), 2-(7-chloro-1,8-naphthyridin-2-yl)-3-(2-diethylaminoethylamino)carbonyloxy-isoindolin-1-one (8 g.), melting at 167° C., is obtained after two recrystallisations from isopropanol.

EXAMPLE 5

Following the procedure of Example 1 but starting with 2-(7-chloro-1,8-naphthyridin-2-yl)-3-phenoxycarbonyloxy-isoindolin-1-one (8.6 g.) and a 33% (w/v) aqueous solution of ethylamine ($d$ = 0.92; 9 cc.) in acetonitrile (200 cc.), 2-(7-chloro-1,8-naphthyridin-2-yl)-3-ethylaminocarbonyloxy-isoindolin-1-one (4.1 g.), melting at 212°–215° C., is obtained.

EXAMPLE 6

Following the procedure of Example 1 but starting with 2-(7-chloro-1,8-naphthyridin-2-yl)-3-phenoxycarbonyloxy-isoindolin-1-one (8.6 g.) and a 40% (w/v) aqueous solution of propylamine (8.75 cc.) in acetonitrile (200 cc.), 2-(7-chloro-1,8-naphthyridin-2-yl)-3-propylaminocarbonyloxy-isoindolin-1-one (4.7 g.), melting at 208°–209° C., is obtained.

EXAMPLE 7

A mixture of 2-(7-chloro-1,8-naphthyridin-2-yl)-3-phenoxycarbonyloxy-isoindolin-1-one (8.6 g.) and sec-butylamine (40 cc.) is heated at 65° C. until dissolution. The reaction mixture is then diluted with diisopropyl ether (240 cc.). The precipitate formed is filtered off and recrystallised from acetonitrile (60 cc.). 2-(7-Chloro- 1,8-naphthyridin-2-yl)-3-sec-butylaminocarbonyloxy-isoindolin-1-one (3 g.), melting at 220°–222° C., is thus obtained.

EXAMPLE 8

Following the procedure of Example 1 but starting with 2-(7-chloro-1,8-naphthyridin-2-yl)-3-phenoxycarbonyloxy-isoindolin-1-one (8.6 g.) and pentylamine (5.2 g.) in acetonitrile (200 cc.), 2-(7-chloro-1,8-naphthyridin-2-yl)-3-pentylaminocarbonyloxy-isoindolin-1-one (4 g.), melting at 150°–151° C., is obtained.

EXAMPLE 9

Cyclopropylamine (2.85 g.) is added to a suspension of 2-(7-chloro-1,8-naphthyridin-2-yl)-3-phenoxycarbonyloxy-isoindolin-1-one (4.3 g.) in acetonitrile (43 cc.), and the suspension obtained is stirred for 20 hours at a temperature of about 20° C. Diisopropyl ether (85 cc.) is then added, after which the insoluble product is filtered off and washed with diisopropyl ether (2 × 10 cc.). Recrystallisation from acetonitrile (130 cc.) gives 2-(7-chloro-1,8-naphthyridin-2-yl)-3-cyclopropylaminocarbonyloxy-isoindolin-1-one (3.2 g.) melting at 220° C.

EXAMPLE 10

Following the procedure of Example 9 but starting with 2-(7-chloro-1,8-naphthyridin-2-yl)-3-phenoxycarbonyloxy-isoindolin-1-one (4.3 g.) and cyclohexylamine (4.95 g.) in acetonitrile (43 cc.), 2-(7-chloro-1,8-naphthyridin-2-yl)-3-cyclohexylaminocarbonyloxy-isoindolin-1-one (2.5 g.), melting at 216° C., is obtained after recrystallisation from acetonitrile.

EXAMPLE 11

Following the procedure of Example 9 but starting with 2-(7-chloro-1,8-naphthyridin-2-yl)-3-phenoxycarbonyloxy-isoindolin-1-one (4.3 g.) and cyclopentylamine (4.25 g.) in acetonitrile (43 cc.), 2-(7-chloro-1,8-naphthyridin-2-yl)-3-cyclopentylaminocarbonyloxy-isoindolin-1-one (2.5 g.), melting at 238° C., is obtained after recrystallisation from acetonitrile.

EXAMPLE 12

Following the procedure of Example 1 but starting with 2-(7-chloro-1,8-naphthyridin-2-yl)-3-phenoxycarbonyloxy-isoindolin-1-one (4.3 g.) and allylamine (2.85 g.) in acetonitrile (43 cc.), 2-(7-chloro-1,8-naphthyridin-2-yl)-3-allylaminocarbonyloxyisoindolin-1-one (2.5 g.), melting at 202° C., is obtained after recrystallisation from acetonitrile.

EXAMPLE 13

Following the procedure of Example 1 but starting with 2-(7-chloro-1,8-naphthyridin-2-yl)-3-phenoxycarbonyloxy-isoindolin-1-one (4.3 g.) and 2-methoxyethylamine (3.75 g.) in acetonitrile (43 cc.), 2-(7-chloro-1,8-naphthyridin-2-yl)-3-(2-methoxyethyl)-aminocarbonyloxy-isoindolin-1-one (2.5 g.), melting at 172° C., is obtained after recrystallisation from acetonitrile.

EXAMPLE 14

Following the procedure of Example 1 but starting with 2-(7-chloro-1,8-naphthyridin-2-yl)-3-phenoxycarbonyloxy-isoindolin-1-one (8.6 g.) and n-hexylamine (6.06 g.) in acetonitrile (200 cc.), 2-(7-chloro-1,8-naphthyridin-2-yl)-3-n-hexylaminocarbonyloxy-isoindolin-1-one (3.2 g.), melting at 145°–146° C., is obtained after recrystallisation from acetonitrile (50 cc.).

EXAMPLE 15

A suspension of 2-(7-chloro-1,8-naphthyridin-2-yl)-3-phenoxycarbonyloxy-isoindolin-1-one (8.62 g.) in a 40% (w/v) aqueous solution of dimethylamine (6.8 cc.) and acetonitrile (200 cc.) is stirred for 4 hours at a temperature of about 20° C. The precipitate is filtered off.

The filtrate is diluted by adding water (900 cc.). The fresh precipitate which forms is filtered off and dried. The two combined precipitates are dissolved in methylene chloride (500 cc.) and the solution is filtered through a column of silica (110 g.) contained in a 3 cm. diameter tube. Elution is carried out with the same solvent and the corresponding eluates are then concentrated to dryness. The residue is then recrystallised from isopropanol (250 cc.) to give 2-(7-chloro-1,8-naphthyridin-2-yl)-3-dimethylaminocarbonyloxy-isoindolin-1-one (2.86 g.) melting at 217°–218° C.

EXAMPLE 16

3-Dimethylamino-n-propylamine (2.26 g.) is added to a suspension of 2-(7-chloro-1,8-naphthyridin-2-yl)-3-phenoxycarbonyloxy-isoindolin-1-one (4.31 g.) in acetonitrile (100 cc.). The mixture is stirred for 2 hours at a temperature of about 20° C. and decolourising charcoal (0.4 g.) is then added. After filtration, water (300 cc.) is added to the filtrate. The solid which forms is filtered off. This gives a crude product (3.4 g.) which is purified by chromatography on silica (30 g.) contained in a column of 3 cm. diameter. Elution is carried out first with methylene chloride (13 × 50 cc.) and then with a mixture (12 × 50 cc.) of methylene chloride and ethyl acetate (1-1 by volume). All the eluates are discarded. Finally, elution is carried out with a mixture (24 × 50 cc.) of ethyl acetate and methanol (1-1 by volume). These last fractions are combined and concentrated to dryness under reduced pressure (20 mm.Hg). The residue is recrystallised from isopropanol (25 cc.). This gives 2-(7-chloro-1,8-naphthyridin-2-yl)-3-(3-dimethylaminopropylamino)carbonyloxy-isoindolin-1-one (2.1 g.) melting at 162° C.

EXAMPLE 17

A mixture of 2-(7-chloro-1,8-naphthyridin-2-yl)-3-phenoxycarbonyloxy-isoindolin-1-one (8.6 g.) and isobutylamine (40 cc.) is heated at 60° C. until dissolution. After cooling, diisopropyl ether (120 cc.) is added. The precipitate is filtered off and washed with diisopropyl ether (15 cc.). After recrystallisation from ethyl acetate (60 cc.), 2-(7-chloro-1,8-naphthyridin-2-yl)-3-isobutylaminocarbonyloxy-isoindolin-1-one (1.8 g.), melting at 200°–202° C., is obtained.

EXAMPLE 18

A suspension of 2-(7-chloro-1,8-naphthyridin-2-yl)-3-phenoxycarbonyloxy-isoindolin-1-one (4.3 g.) and N,N,N'-trimethylethylenediamine (3.1 g.) in acetonitrile (100 cc.) is stirred for 18 hours. The mixture is then heated at the reflux temperature for 30 minutes, after which it is left to stand for 24 hours. A solid product separates out and is filtered off and dried.

The filtrate is concentrated to dryness and the residue (5 g.) is purified by chromatography on silica (100 g.), contained in a column of 3 cm. diameter, in ethyl acetate. Elution is carried out successively with ethyl acetate (5 × 100 cc.); the eluates are discarded. Afterwards elution is effected with a mixture (8 × 100 cc.) of ethyl acetate and methanol (1-1 by volume). These last eight fractions are evaporated under reduced pressure and the residue is combined with the first product isolated by filtration and then dissolved in methylene chloride (100 cc.). The organic phase is washed with water (75 cc.), dried over potassium carbonate, decolourised with charcoal and filtered.

The filtrate, when evaporated to dryness, leaves a solid residue which is triturated with diisopropyl ether (25 cc.) and then with water (50 cc.). The product is filtered off and dried. This gives 2-(7-chloro-1,8-naphthyridin-2-yl)-3-[(2-N-dimethylaminoethyl)-N-methylamino]carbonyloxy-isoindolin-1-one (1.2 g.) melting at 174°–176° C.

N,N,N'-Trimethylethylenediamine can be prepared in accordance with the method of J. von Braun, K. Heider and F. Muller, Chem. Ber., 51, 737 (1918).

EXAMPLE 19

Following the procedure of Example 1 but starting with 2-(7-chloro-1,8-naphthyridin-2-yl)-3-phenoxycarbonyloxy-isoindolin-1-one (4.3 g.) and benzylamine (4.28 g.) in acetonitrile (45 cc.), 2-(7-chloro-1,8-naphthyridin-2-yl)-3-benzylaminocarbonyloxy-isoindolin-1-one (2.95 g.), melting at 180° C., is obtained after recrystallisation from acetonitrile (40 cc.).

EXAMPLE 20

A solution of piperidine (3.06 g.) in anhydrous dimethylformamide (5 cc.) is added to a suspension of 6-(7-chloro-1,8-naphthyridin-2-yl)-7-oxo-5-phenoxycarbonyloxy-6,7-dihydro-5H-pyrrolo[3,4-b]pyrazine (5.2 g.) in anhydrous dimethylformamide (21 cc.). The reaction mixture is stirred for 15 minutes at a temperature of about 25° C., after which diisopropyl ether (75 cc.) is added. The insoluble product is filtered off, washed with diisopropyl ether (4 × 10 cc.) and then treated with methylene chloride (100 cc.). A slight amount of insoluble matter is filtered off, and the organic solution obtained is then washed by twice successively decanting it with 1N sodium hydroxide solution (25 cc.) and water (25 cc.), dried over anhydrous sodium sulphate and evaporated to dryness under reduced pressure. After recrystallising the residue obtained from acetonitrile (130 cc.), 6-(7-chloro-1,8-naphthyridin-2-yl)-7-oxo-5-piperidinocarbonyloxy-6,7-dihydro-5H-pyrrolo[3,4-b]pyrazine (2.25 g.), melting at 249° C., is obtained.

6-(7-Chloro-1,8-naphthyridin-2-yl)-7-oxo-5-phenoxycarbonyloxy-6,7-dihydro-5H-pyrrolo[3,4-b]pyrazine can be prepared by adding phenyl chloroformate (9.4 g.) to a suspension of 6-(7-chloro-1,8-naphthyridin-2-yl)-5-hydroxy-7-oxo-6,7-dihydro-5H-pyrrolo[3,4-b]pyrazine (6.3 g.) in anhydrous pyridine (63 cc.) whilst stirring and keeping the temperature at about 5° C. When the addition is complete, the reaction mixture is heated gradually to 60° C. and this temperature is maintained for 1 hour. After cooling, the reaction mixture is poured into distilled water (350 cc.) whilst keeping the temperature at about 10° C. The insoluble product is filtered off and washed successively with water (120 cc.), acetonitrile (40 cc.) and diisopropyl ether (40 cc.). After drying, 6-(7-chloro-1,8-naphthyridin-2-yl)-7-oxo-5-phenoxycarbonyloxy-6,7-dihydro-5H-pyrrolo[3,4-b]pyrazine (7.2 g.), melting at 270° C., is obtained.

6-(7-Chloro-1,8-naphthyridin-2-yl)-5-hydroxy-7-oxo-6,7-dihydro-5H-pyrrolo[3,4-b]pyrazine can be prepared by adding potassium borohydride (0.97 g.) to a suspension of 6-(7-chloro-1,8-naphthyridin-2-yl)-5,7-dioxo-6,7-dihydro-5H-pyrrolo[3,4-b]pyrazine (7.45 g.) in a mixture (288 cc.) of dioxan and methanol (50-50 by volume), whilst stirring and keeping the temperature at about 3° C. After stirrng for 2 hours at this temperature, the insoluble product is filtered off and washed successively with a mixture (24 cc.) of dioxan and methanol (50-50 by volume), water (24 cc.), a mixture (24 cc.) of dioxan and methanol (50-50 by volume) and diisopropyl ether (12 cc.). After drying, 6-(7-chloro-1,8-naphthyridin-2-yl)-5-hydroxy-7-oxo-6,7-dihydro-5H-pyrrolo[3,4-b]pyrazine (5.3 g.), melting at 270° C. with decomposition, is obtained.

6-(7-Chloro-1,8-naphthyridin-2-yl)-5,7-dioxo-6,7-dihydro-5H-pyrrolo[3,4-b]pyrazine can be prepared by adding 6-(7-hydroxy-1,8-naphthyridin-2-yl)-5,7-dioxo-6,7-dihydro-5H-pyrrolo[3,4-b]pyrazine (32 g.) gradually to a solution of dimethylformamide (3.8 cc.) in phosphorus oxychloride (128 cc.) at a temperature of about 15° C. When the addition is complete, the reaction mixture is heated at the reflux temperature for half an hour and is then cooled and poured in small portions onto crushed ice (1.3 kg.). The insoluble product is filtered off and washed with water until the wash liquors are at pH 5. After drying, 6-(7-chloro-1,8-naphthyridin-2-yl)-5,7-dioxo-6,7-dihydro-5H-pyrrolo[3,4-b]pyrazine (21.3 g.), melting at about 340° C. with decomposition, is obtained.

6-(7-Hydroxy-1,8-naphthyridin-2-yl)-5,7-dioxo-6,7-dihydro-5H-pyrrolo[3,4-b]pyrazine can be prepared by heating to the reflux temperature a suspension of 2-amino-7-hydroxy-1,8-naphthyridine (22.4 g.) and pyrazine-2,3-dicarboxylic acid anhydride (23 g.) in acetic acid (280 cc.). After refluxing for 1 hour, the reaction mixture is cooled to a temperature of about 30° C. and acetic anhydride (280 cc.) is added. The reaction mixture is again heated at the reflux temperature for 10 minutes and then cooled to a temperature of about 20° C. The insoluble product is filtered off and washed with acetic acid (40 cc.) and diisopropyl ether (200 cc.). After drying, 6-(7-hydroxy-1,8-naphthyridin-2-yl)-5,7-dioxo-6,7-dihydro-5H-pyrrolo[3,4-b]pyrazine (32.1 g.), melting at 373° C., is obtained.

2-Amino-7-hydroxy-1,8-naphthyridine can be prepared according to the method described by S. Carboni et al., Gazz. Chim. Ital., 95, 1498 (1965).

EXAMPLE 21

Pyridine (10 cc.), triethylamine (5 cc.) and dimethylcarbamoyl chloride (1.61 g.) are added successively to a suspension of 2-(7-chloro-1,8-naphthyridin-2-yl)-3-hydroxy-isoindolin-1-one (3.11 g.) in methylene chloride (50 cc.). The reaction mixture is stirred for 16 hours at a temperature of about 20° C. and water (50 cc.) and methylene chloride (25 cc.) are then added. The aqueous layer is decanted off and washed with methylene chloride (2 × 25 cc.). The organic layers are combined, washed with water (2 × 25 cc.), dried over sodium sulphate and evaporated to dryness under reduced pressure. Recrystallisation of the residue obtained from acetonitrile (45 cc.) gives 2-(7-chloro-1,8-naphthyridin-2-yl)-3-dimethylaminocarbonyloxy-isoindolin-1-one (2.8 g.) melting at 218° C.

EXAMPLE 22

Pyridine (30 cc.), triethylamine (8.4 cc.) and N-chlorocarbonylmorpholine (8.97 g.) are added successively to a suspension of 2-(7-chloro-1,8-naphthyridin-2- yl)-3-hydroxy-isoindolin-1-one (6.2 g.) in methylene chloride (300 cc.). The mixture is stirred for 20 hours at a temperature of about 20° C. and water (250 cc.) is then added. The precipitate is filtered off, then washed with water (30 cc.) and finally dried. After recrystallisation from dimethylformamide (60 cc.), 2-(7-chloro-1,8-naphthyridin-2-yl)-3-[(4- morpholino)carbonyloxy]-isoindolin-1-one (6 g.), melting at 290° C., is obtained.

N-Chlorocarbonylmorpholine can be prepared in accordance with the process described by V. G. Nemetz and J. P. Kurlina, Arb. Leningrader chem.-technol. Rote-Fahne-Inst. Leningrader Rates, 10, 3 (1941) [Chemisches Zentralblatt, II, 2088 (1941)].

EXAMPLE 23

The procedure of Example 21 is followed but starting with 2-(7-chloro-1,8-naphthyridin-2-yl)-3-hydroxy-isoindolin-1-one (6.2 g.) in methylene chloride (300 cc.), diethylcarbamoyl chloride (8.15 g.), triethylamine (8.4 cc.) and pyridine (30 cc.). Water (250 cc.) is added to the reaction mixture after it has been stirred for 48 hours at a temperature of about 20° C. The precipitate formed is filtered off and recrystallised from diisopropyl ether (800 cc.) to give 2-(7-chloro-1,8-naphthyridin-2-yl)-3-diethylaminocarbonyloxy-isoindolin-1-one (4.7 g.) melting at 142°–144° C.

Diethylcarbamoyl chloride can be prepared in accordance with the process described by W. R. Boon, J. Chem. Soc., 307 (1947).

EXAMPLE 24

The procedure of Example 21 is followed but starting with 2-(7-chloro-1,8-naphthyridin-2-yl)-3-hydroxy-isoindolin-1-one (6.2 g.), N-ethyl-N-methylcarbamoyl chloride (7.3 g.), triethylamine (8.4 cc.) and pyridine (30 cc.) in methylene chloride (300 cc.). After stirring for 24 hours at a temperature of about 20° C., the solvent is evaporated under reduced pressure and the residue is triturated with water (100 cc.). The precipitate is filtered off and dissolved in boiling ethyl acetate (70 cc.) containing decolourising charcoal (0.5 g.). After filtering hot and cooling the solution, the crystals obtained are filtered off and dried. This gives 2-(7-chloro-1,8-naphthyridin-2-yl)-3-(N-methyl-N-ethylaminocarbonyloxy)-isoindolin-1-one (5.2 g.) melting at 184° C.

N-Ethyl-N-methylcarbamoyl chloride can be prepared in the following manner:

A 2.5N solution (84 cc.) of phosgene in methylcyclohexane is cooled to −10° C. Whilst maintaining this temperature, triethylamine (20.2 g.) is added, followed by a solution of N-methylethylamine (11.8 g.) in toluene (100 cc.). The mixture is kept at 0° C. for 18 hours and the precipitate is then filtered off. The filtrate is concentrated and the residue is distilled rapidly under atmospheric pressure. This gives a crude product (26 g.). After rectification, N-ethyl-N-methylcarbamoyl chloride (16 g.), b.p. 88°–89° C./40 mm.Hg, is finally obtained.

N-Methylethylamine can be prepared by the method of Wawzonek et al., Org. Synth., 44, 75 (1964).

EXAMPLE 25

The procedure of Example 21 is followed but starting with 2-(7-chloro-1,8-naphthyridin-2-yl)-3-hydroxy-isoindolin-1-one (6.2 g.), N-methyl-N-n-propylcarbamoyl chloride (8.3 g.), triethylamine (8.4 cc.) and pyridine (30 cc.) in methylene chloride (300 cc.). After concentrating the mixture, the residue is taken up in water (100 cc.). The precipitate formed is filtered off, drained, dried and then recrystallised from ethyl acetate (80 cc.). This gives 2-(7-chloro-1,8-naphthyridin-2-yl)-3-(N-methyl-N-propylaminocarbonyloxy)-isoindolin-1-one (5.7 g.) melting at 180° C.

N-Methyl-N-propylcarbamoyl chloride can be prepared from a 2.5N solution (840 cc.) of phosgene in methylcyclohexane, triethylamine (20.2 g.) and N-methyl-propylamine (14.6 g.) in toluene (100 cc.). N-Methyl-N-propylcarbamoyl chloride (18 g.), b.p. 100° C./40 mm.Hg, is thus obtained.

N-Methylpropylamine can be prepared in accordance with the method described by J. von Braun et al., Chem. Ber., 61, 1427 (1928).

EXAMPLE 26

The procedure of Example 21 is followed, but starting with 2-(7-chloro-1,8-naphthyridin-2-yl)-3-hydroxy-isoindolin-1-one (6.2 g.), N-n-butyl-N-methylcarbamoyl chloride (9 g.), triethylamine (8.4 cc.) and pyridine (30 cc.) in methylene chloride (300 cc.). The solution is concentrated to dryness and the residue is taken up in water (300 cc.). The precipitate, which is filtered off, is recrystallised from a boiling mixture (90 cc.) of ethyl acetate and diisopropyl ether (1-1 by volume). Decolourising charcoal (0.5 g.) is added and the mixture is filtered hot. After cooling, the crystals obtained are filtered off and dried. This gives 2-(7-chloro-1,8-naphthyridin-2-yl)-3-(N-butyl-N-methylaminocarbonyloxy)-isoindolin-1-one (4.2 g.) melting at 148° C.

N-Butyl-N-methylcarbamoyl chloride can be prepared from a 2.5N solution (126 cc.) of phosgene in methylcyclohexane, triethylamine (30.3 g.) and N-methylbutylamine (26.1 g.) in toluene (150 cc.). This gives N-butyl-N-methylcarbamoyl chloride (27.5 g.), b.p. 110°–111° C./35 mm.Hg.

EXAMPLE 27

The procedure of Example 21 is followed but starting with 2-(7-chloro-1,8-naphthyridin-2-yl)-3-hydroxy-isoindolin-1-one (6.2 g.), dibutylcarbamoyl chloride (1.5 g.), triethylamine (8.4 cc.) and pyridine (30 cc.) in methylene chloride (300 cc.). Water (250 cc.) is added to the reaction mixture and the organic phase is decanted. The aqueous phase is extracted with methylene chloride (250 cc.). The combined organic extracts are dried over anhydrous sodium sulphate (15 g.), filtered and concentrated to dryness. The residue is triturated in diisopropyl ether (100 cc.). The precipitate formed is filtered off and then chromatographed on silica (80 g.), contained in a column of 4 cm. diameter, in methylene chloride. Elution is carried out successively with methylene chloride (5 × 100 cc.) and with a mixture (2 × 100 cc.) of methylene chloride and ethyl acetate (8-2 by volume).

The last two fractions are evaporated under reduced pressure and the residue is recrystallised from diisopropyl ether (140 cc.). This gives 2-(7-chloro-1,8-naphthyridin-2-yl)-3-N,N-dibutylaminocarbonyloxy-isoindolin-1-one (2.2 g.) melting at 136°–138° C.

Dibutylcarbamoyl chloride can be prepared in accordance with the process described by F. A. Werner, J. Chem. Soc., 115, 1013 (1919).

EXAMPLE 28

N-Methyl-N-n-pentylcarbamoyl chloride (5.6 g.), triethylamine (4.7 cc.) and pyridine (15 cc.) are added to a solution of 2-(7-chloro-1,8-naphthyridin-2-yl)-3-hydroxy-isoindolin-1-one (3.5 g.) in methylene chloride (150 cc.). After 72 hours at a temperature of about 20° C., the reaction mixture is concentrated under reduced pressure (300 mm.Hg). Water (200 cc.) is added to the residue. The precipitate is filtered off and then washed with water (30 cc.) and diethyl ether (30 cc.). After recrystallisation from a mixture (30 cc.) of ethyl acetate and diisopropyl ether (1-1 by volume), 2-(7-chloro-1,8-naphthyridin-2-yl)-3-(N-methyl-N-pentylaminocarbonyloxy)-isoindolin-1-one (3.6 g.), melting at 135°–136° C., is obtained.

N-Methyl-N-pentylcarbamoyl chloride can be prepared as follows:

Triethylamine (14 cc.) is added over the course of 8 minutes to a 2.5N solution (42 cc.) of phosgene in methylcyclohexane, cooled to −10° C., and a solution of N-methylpentylamine (13.7 cc.) in toluene (50 cc.) is then added whilst maintaining the temperature at −10° C. The mixture is stirred for 1 hour at +5° C. The insoluble material is then filtered off and washed with toluene (80 cc.). The organic solutions are dried over calcium chloride (10 g.). After filtration, the solvents are evaporated under reduced pressure (40 mm.Hg). The residue is distilled under reduced pressure to give N-methyl-N-pentylcarbamoyl chloride (5.6 g.), b.p. 120–125° C./40 mm.Hg.

EXAMPLE 29

Dimethylcarbamoyl chloride (4.85 g.) and triethylamine (4.55 g.) are added successively to a suspension of 6-(7-chloro-1,8-naphthyridin-2-yl)-5-hydroxy-7-oxo-6,7-dihydro-5H-pyrrolo[3,4-b]pyrazine (4.7 g.) in a mixture of anhydrous methylene chloride (47 cc.) and anhydrous pyridine (16 cc.). The reaction mixture is heated at the reflux temperature for 2 hours, and is then cooled and poured into water (180 cc.). A slight amount of insoluble matter is filtered off and the aqueous layer is decanted off and washed with methylene chloride (2 × 50 cc.) by successive decantations. The combined organic layers are washed by successive decantations with 1N sodium hydroxide solution (2 × 30 cc.) and water (2 × 33 cc.), dried with anhydrous sodium sulphate in the presence of decolourising charcoal, filtered and evaporated to dryness under reduced pressure. The residue obtained is taken up in acetonitrile (20 cc.) and the insoluble product is filtered off and washed with acetonitrile (3 × 2 cc.). Recrystallisation of this product from dimethylformamide (14 cc.) gives a solvated product (4.1 g.). This product is dissolved in dimethylformamide (100 cc.) at a temperature of about 70° C. The solution thus obtained is poured into water (1,200 cc.) and the insoluble product is filtered off and washed with water (5 × 20 cc.). After drying, 6-(7-chloro-1,8-naphthyridin-2-yl)-5-dimethylaminocarbonyloxy-7-oxo-6,7-dihydro-5H-pyrrolo[3,4-b]pyrazine (3.6 g.), melting at 270° C., is obtained.

EXAMPLE 30

Following the procedure of Example 29 but starting with 6-(7-chloro-1,8-naphthyridin-2-yl)-5-hydroxy-7-oxo-6,7-dihydro-5H-pyrrolo[3,4-b]pyrazine (4.7 g.) and N-butyl-N-methylcarbamoyl chloride (6.23 g.) in a mixture of methylene chloride (47 cc.) and pyridine (16 cc.) in the presence of triethylamine (4.55 g.), 6-(7-chloro-1,8-naphthyridin-2-yl)-5-N-butyl-N-methylaminocarbonyloxy-7-oxo-6,7-dihydro-5H-pyrrolo[3,4-b]pyrazine (3.9 g.), melting at 234° C., is obtained after recrystallisation from acetonitrile (65 cc.).

EXAMPLE 31

A mixture of 2-(7-chloro-1,8-naphthyridin-2-yl)-3-hydroxy-isoindolin-1-one (1.56 g.) and n-butyl isocyanate (0.99 g.) in anhydrous acetonitrile (30 cc.) is heated at the reflux temperature for 2 hours. The solution obtained is treated with decolourising charcoal at the reflux temperature, filtered hot, after which it is cooled to a temperature of about 20° C. The product which crystallises is filtered off and washed with acetonitrile (4 cc.). After drying, 2-(7-chloro-1,8 naphtyridin-2-yl)-3-n-butylaminocarbonyloxy-isoindolin-1-one (0.96 g.), melting at 152° C. and then at 174° C., is obtained.

EXAMPLE 32

A suspension of 2-(7-chloro-1,8-naphthyridin-2-yl)-3-hydroxy-isoindolin-1-one (3.2 g.), methyl 2-isocyanatoacetate (1.4 g.) and triethylamine (1.2 g.) in acetonitrile (50 cc.) is stirred for 18 hours at a temperature of about 20° C. A further amount of methyl 2-isocyanatoacetate (0.7 g.) is added and stirring is continued for a further 3 hours. The precipitate is filtered off and is dissolved in methylene chloride (35 cc.). Decolourising charcoal (0.5 g.) is added. After filtration, diisopropyl ether (105 cc.) is added to the filtrate. The crystalline precipitate which forms is filtered off, washed with diisopropyl ether (15 cc.) and then dried to give 2-(7-chloro-1,8-naphthyridin-2-yl)-3-methoxycarbonylmethylaminocarbonyloxy-isoindolin-1-one (2.5 g.) melting at 208°–210° C.

Methyl 2-isocyanatoacetate can be prepared in accordance with the process described by M. H. Benn et al., J. Chem. Soc., 2365 (1961).

EXAMPLE 33

Pyridine (10 cc.) and n-butyl isocyanate (11.2 cc.) are added to a suspension of 2-(7-chloro-1,8-naphthyridin-2-yl)-3-hydroxy-5-trifluoromethyl-isoindolin-1-one (3.8 g.) in acetonitrile (380 cc.). The mixture is heated to the reflux temperature and triethylamine (0.5 cc.) is then added. Refluxing is continued for 1 hour and 30 minutes until dissolution. The reaction mixture is then concentrated under reduced pressure (40 mm.Hg), and the residue is recrystallised from acetonitrile (48 cc.) to give 3-n-butylaminocarbonyloxy-2-(7-chloro-1,8-naphthyridin-2-yl)-5-trifluoromethyl-isoindolin-1-one (3.5 g.) melting at 120° C. and then at 176° C.

2-(7-Chloro-1,8-naphthyridin-2-yl)-3-hydroxy-5-trifluoromethyl-isoindolin-1-one and its isomer 2-(7-chloro-1,8-naphthyridin-2-yl)-3-hydroxy-6-trifluoromethyl-isoindolin-1-one can be prepared as follows:

Potassium borohydride (12 g.) is added at a temperature of 15°–18° C. to a suspension of 5-trifluoromethyl-N-(7-chloro-1,8-naphthyridin-2-yl)-phthalimide (83.6 g.) in methanol (420 cc.) and dioxan (420 cc.). The mixture is stirred for a further 2 hours and is then cooled externally by means of an ice bath. The precipitate formed is filtered off and washed with a mixture (40 cc.) of methanol and dioxan (1-1 by volume). The precipitate is filtered off, dried and then stirred for 30 minutes with the same mixture (200 cc.); thereafter the precipitate is filtered off and heated with ethanol (200 cc.) to the reflux temperature. After cooling the suspension and filtering it, 2-(7-chloro-1,8-naphthyridin-2-yl)-3-hydroxy-5-trifluoromethyl-isoindolin-1-one (21.9 g.), melting at a temperature above 300° C., is obtained.

The solution obtained after filtering the reaction mixture and the liquors from the washes with the methanol-dioxan mixture are combined. Water (2,500 cc.) is added. The precipitate which forms is filtered off, washed with water (600 cc.) and recrystallised twice from a mixture of methanol and dioxan (5-5 by volume). This gives 2-(7-chloro-1,8-naphthyridin-2-yl)-3-hydroxy-6-trifluoromethyl-isoindolin-1-one (15.3 g.) melting at 265° C.

5-Trifluoromethyl-N-(7-chloro-1,8-naphthyridin-2-yl)-phthalimide can be prepared in the following manner:

4-Trifluoromethylphthalic anhydride (73.5 g.) and N-hydroxysuccinimide (50.2 g.) in dimethylformamide (1,500 cc.) are heated at 75°–78° C. for 18 hours. 2-Amino-7-chloro-1,8-naphthyridine (61.4 g.) and N,N'-dicyclohexylcarbodiimide (140 g.) are then added and the mixture is heated for a further 3 hours at the same temperature. After cooling, the precipitate formed is filtered off and washed with dimethylformamide (100 cc.) and then with diisopropyl ether (200 cc.).

Water (1,500 cc.) is added to the reaction mixture. The precipitate which forms is filtered off and washed with methylene chloride (1,500 cc.). The two combined precipitates are washed with methylene chloride (8 liters). The filtrate is freed from insoluble matter by filtration and is then concentrated to dryness to give 5-trifluoromethyl-N-(7-chloro-1,8-naphthyridin-2-yl)-phthalimide (83.6 g.), melting at 265° C.

4-Trifluoromethylphthalic anhydride can be prepared in the following manner:

4-Trifluoromethylphthalic acid (106.6 g.) and acetic anhydride (215 cc.) are heated at the reflux temperature for 30 minutes. After concentrating the mixture under reduced pressure (30 mm.Hg), the residue is stirred with cyclohexane (420 cc.). After filtration and drying, 4-trifluoromethylphthalic anhydride (73.5 g.), melting at 54° C., is obtained.

4-Trifluoromethylphthalic acid can be prepared in the following manner:

Methyl 2-cyano-4-trifluoromethylbenzoate (102.3 g.), sodium hydroxide pellets (108 g.), water (900 cc.) and methanol (1,900 cc.) are heated at the reflux temperature for 12 hours. The solution is decolourised with decolourising charcoal (0.6 g.). After filtering, hydrochloric acid (d = 1.19; 100 cc.) is added. The mixture is extracted with diethyl ether (2.25 liters). The organic layer is dried over anhydrous magnesium sulphate (40 g.). After filtering, and concentrating the filtrate, 4-trifluoromethylphthalic acid (99.1 g.), melting at 178° C., is obtained.

Methyl 2-cyano-4-trifluoromethylbenzoate can be prepared in the following manner:

Methyl 2-amino-4-trifluoromethylbenzoate (144.6 g.) is suspended in a mixture of ice (1.3 kg.), water (730 cc.) and hydrochloric acid (d = 1.19; 171.5 cc.). A solution of sodium nitrite (49.9 g.) in water (172 cc.) is added, all at once, to the solution obtained. The reaction mixture is stirred for 2 hours 30 minutes at 0°–1° C. and is filtered and then added dropwise, over the course of 1 hour 20 minutes, to a solution, kept at 4°–5° C., of copper sulphate (226 g.) and potassium cyanide (261 g.) in water (1,320 cc.) [a solution prepared according to Gabriel, Ber., 52, 1089 (1919)]. During the addition of the solution of the diazo compound, the pH is kept at 6–7 by addition of a 10% sodium carbonate solution. Stirring is continued whilst allowing the temperature to rise to 20° C. The mixture is then extracted with diethyl ether (3 liters). The ether layer is washed with water (150 cc.) and dried over anhydrous magnesium sulphate (30 g.). After filtering and concentrating the solution, methyl 2-cyano-4-trifluoromethylbenzoate (94.9 g.), melting at 52° C., is obtained.

Methyl 2-amino-4-trifluoromethylbenzoate can be prepared as follows:

2-Amino-4-trifluoromethylbenzoic acid (141.2 g.), methanol (1.51 liters) and boron trifluoride etherate (506 cc.) are heated at the reflux temperature for 99 hours. The solution obtained is added to sodium carbonate (350 g.) in ice-water (2.8 kg.). The mixture is stirred for 15 minutes and is then extracted with diethyl ether (3 liters). The ether layer is washed with water (250 cc.) and then dried over anhydrous magnesium sulphate (30 g.). After filtering and concentrating the solution, methyl 2-amino-4-trifluoromethylbenzoate (137 g.), melting at 64° C., is obtained.

2-Amino-4-trifluoromethylbenzoic acid can be prepared in accordance with the method of Hauptschein et al., J. Amer. Chem. Soc., 76, 1051 (1954).

EXAMPLE 34

Pyridine (10 cc.) and butyl isocyanate (11.2 cc.) are added to a suspension of 2-(7-chloro-1,8-naphthyridin-2-yl)-3-hydroxy-6-trifluoromethyl-isoindolin-1-one (3.8 g.) in acetonitrile (380 cc.). The mixture is heated to the reflux temperature and triethylamine (0.5 cc.) is added. Refluxing is continued for 50 minutes until dissolution. After cooling the solution, the precipitate formed is filtered off and washed with water (30 cc.). After drying, a first crop of 2-(7-chloro-1,8-naphthyridin-2-yl)-3-n-butylaminocarbonyloxy-6-trifluoromethyl-isoindolin-1-one (2.8 g.) is obtained.

The mother liquors are concentrated to dryness. The residue is taken up in water (30 cc.). The precipitate formed is filtered off, washed with acetonitrile (20 cc.) and recrystallised from acetone (40 cc.). A second crop (0.6 g.) is thus obtained. The two crops are combined and then recrystallised from acetonitrile (140 cc.). This gives 2-(7-chloro-1,8-naphthyridin-2-yl)-3-n-butylaminocarbonyloxy-6-trifluoromethyl-isoindolin-1-one (3 g.) melting at 245° C.

EXAMPLE 35 n-Butyl isocyanate (11.2 cc.) is added over the course of 15 minutes to a suspension of 5-chloro-2-(7-chloro-1,8-naphthyridin-2-yl)-3-hydroxy-isoindolin-1-one (3.5 g.) in acetonitrile (350 cc.) and triethylamine (0.2 cc.) heated at the reflux temperature. Pyridine (10 cc.) and triethylamine (5 cc.) are added and refluxing is continued for a further 40 minutes. After filtering hot and then cooling, the precipitate formed is filtered off and recrystallised from acetonitrile (250 cc.) to give 5-chloro-2-(7-chloro-1,8-naphthyridin-2-yl)-3-n-butylaminocarbonyloxy-isoindolin-1-one (3.3 g.) melting at 228°–230° C.

5-Chloro-2-(7-chloro-1,8-naphthyridin-2-yl)-3-hydroxy-isoindolin-1-one can be prepared as follows:

Preparation of 4-chlorophthalic anhydride (m.p. 96° C.) according to E. E. Ayling, J. Chem. Soc., 1929, 253.

Preparation of 2-amino-7-hydroxy-1,8-naphthyridin (m.p. 300°–305° C.) according to S. Carboni et al., Ann. Chim. (Roma), 54, 883 (1964).

Preparation of 2-(7-hydroxy-1,8-naphthyridin-2-yl)-5-chlorophthalimide (7 g.) (m.p. 320° C.) by reaction of 2-amino-7-hydroxy-1,8-naphthyridine (9.5 g.) with 4- chlorophthalic anhydride (21.5 g.) in acetic acid (450 cc.) for 1 hour at 116° C.

Preparation of 2-(7-chloro-1,8-naphthyridin-2-yl)-5-chlorophthalimide (6.4 g.) (m.p. 280° C.) by reaction of phosphorus oxychloride (70 cc.) with 2-(7-hydroxy-1,8-naphthyridin-2-yl)-5-chlorophthalimide (7 g.) in the presence of dimethylformamide (0.7 cc.).

Reaction of potassium borohydride (0.75 g.) with 2-(7-chloro-1,8-naphthyridin-2-yl)-5-chlorophthalimide (6.4 g.) in a mixture (300 cc.) of dioxan and methanol (50-50 by volume) gives a mixture (5.2 g.) of 2-(7-chloro-1,8-naphthyridin-2-yl)-5-chloro-3-hydroxy-isoindolin-1-one and of 2-(7-chloro-1,8-naphthyridin-2-yl)-6-chloro-3-hydroxy-isoindolin-1-one. This mixture is twice recrystallised from dichloroethane (700 cc. and then 315 cc.). This gives a product (1.51 g.), which is recrystallised successively from bromoform (38 cc.) and then from a mixture (104.5 cc.) of dichloroethane and ethanol (91-9 by volume) to give 5-chloro-2-(7-chloro-1,8-naphthyridin-2-yl)-3-hydroxy-isoindolin-1-one (0.65 g.).

EXAMPLE 36 n-Butyl isocyanate (5 g.) is added to a suspension of 6-(7-chloro-1,8-naphthyridin-2-yl)-5-hydroxy-7-oxo-6,7-dihydro-5H-pyrrolo[3,4-b]pyrazine (7.8 g.) in anhydrous acetonitrile (156 cc.) and the mixture is heated at the reflux temperature for 7 hours. The insoluble product is filtered off and washed with anhydrous acetonitrile (2 × 10 cc.). The product obtained is dissolved in methylene chloride (430 cc.) and the resulting solution is washed by successive decantations with 0.1N sodium hydroxide solution (85 cc.) and water (85 cc.). After drying, the organic phase is concentrated to dryness under reduced pressure (20 mm.Hg). Recrystallisation of the residue obtained, from acetonitrile (230 cc.), gives 5-n-butylaminocarbonyloxy-6-(7-chloro-1,8-naphthyridin-2-yl)-7-oxo-6,7-dihydro-5H-pyrrolo[3,4-b]pyrazine (5.2 g.) melting at 264° C.

EXAMPLE 37

A suspension of 6-(7-chloro-1,8-naphthyridin-2-yl)-5-hydroxy-7-oxo-6,7-dihydro-5H-pyrrolo[3,4-b]pyridine (1 g.) in acetonitrile (100 cc.) containing n-butyl isocyanate (7.25 cc.) and triethylamine (0.5 cc.) is heated at the reflux temperature for 3 hours. n-Butyl isocyanate (2.9 cc.) and triethylamine (2 drops) are then added and heating at the reflux temperature is continued for a further 30 minutes. After concentrating the mixture to dryness under reduced pressure (40 mm.Hg), the residue is triturated with diisopropyl ether (10 cc.). The precipitate is filtered off and recrystallised from acetonitrile (41 cc.) to give 5-n-butylaminocarbonyloxy-6-(7-chloro-1,8-naphthyridin-2-yl)-7-oxo-6,7-dihydro-5H-pyrrolo[3,4-b]pyridine (0.8 g.) melting at 215° C.

The 6-(7-chloro-1,8-naphthyridin-2-yl)-5-hydroxy-7-oxo-6,7-dihydro-5H-pyrrolo[3,4-b]pyridine starting material can be prepared in the following manner:

Preparation of 2-(7-hydroxy-1,8-naphthyridin-2-yl)-quinolinimide (31.6 g.) (m.p. 364° C.) from 2-amino-7-hydroxy-1,8-naphthyridine (24.2 g.) and quinolinic anhydride (45 g.) in acetic acid (120 cc.) and acetic anhydride (45 cc.) at 130°-135° C. for 1 hour.

Preparation of 2-(7-chloro-1,8-naphthyridin-2-yl)-quinolinimide (11.4 g.) (m.p. 278° C.) from 2-(7-hydroxy-1,8-naphthyridin-2-yl)-quinolinimide (14 g.) in phosphorus oxychloride (80 cc.) and dimethylformamide (2 cc.) for 1 hour at 95°-97° C.

Reduction of 2-(7-chloro-1,8-naphthyridin-2-yl)-quinolinimide (9.8 g.) with potassium borohydride (1.28 g.) in a mixture of dioxan and methanol (50-50 by volume) at a temperature of 10°-15° C. yields a product (7.4 g.) which is chromatographed on alumina (750 g.) contained in a column of 6 cm. diameter. Elution is carried out with chloroform, collecting 700 cc. fractions. The first five fractions yield, after evaporation, 6-(7-chloro-1,8-naphthyridin-2-yl)-7-hydroxy-5-oxo-6,7-dihydro-5H-pyrrolo[3,4-b]pyridine (1.2 g.) melting at 272° C.

The next fraction yields a product (0.9 g.) consisting of a mixture of 6-(7-chloro-1,8-naphthyridin-2-yl)-7-hydroxy-5-oxo-6,7-dihydro-5H-pyrrolo[3,4-b]pyridine and 6-(7-chloro-1,8-naphthyridin-2-yl)-5-hydroxy-7-oxo-6,7-dihydro-5H-pyrrolo[3,4-b]pyridine and the last five fractions, after evaporation, yield 6-(7-chloro-1,8-naphthyridin-2-yl)-5-hydroxy-7-oxo-6,7-dihydro-5H-pyrrolo[3,4-b]pyridine (3.3 g.) melting at a temperature above 300° C.

EXAMPLE 38

A suspension of 6-(7-chloro-1,8-naphthyridin-2-yl)-7-hydroxy-5-oxo-6,7-dihydro-5H-pyrrolo[3,4-b]pyridine (1 g.) in acetonitrile (100 cc.) containing n-butyl isocyanate (7.25 cc.) and triethylamine (0.5 cc.) is heated at the reflux temperature for 1 hour 30 minutes. n-Butyl isocyanate (7.25 cc.) and triethylamine (0.5 cc.) are then added and heating at the reflux temperature is continued for a further 3 hours. The solution is filtered and the filtrate is concentrated under reduced pressure (40 mm.Hg). The residue obtained is triturated with diisopropyl ether (20 cc.). The solid is filtered off and is recrystallised from acetonitrile (35 cc.) to give 7-n-butylaminocarbonyloxy-6-(7-chloro-1,8-naphthyridin-2-yl)-5-oxo-6,7-dihydro-5H-pyrrolo[3,4-b]pyridine (0.96 g.) melting at 215° C.

EXAMPLE 39

Cyclohexyl isocyanate (1.38 g.) is added to a suspension of 6-(7-chloro-1,8-naphthyridin-2-yl)-5-hydroxy-7-oxo-6,7-dihydro-5H-pyrrolo[3,4-b]pyrazine (3.12 g.) in anhydrous acetonitrile (60 cc.) in the presence of triethylamine (1 cc.), and the reaction mixture is heated at the reflux temperature for 13 hours. After cooling, the insoluble product is filtered off and washed successively with acetonitrile (2 × 10 cc.) and diisopropyl ether (2 × 20 cc.). It is then dissolved in methylene chloride (300 cc.) and the solution obtained is stirred for 15 minutes with 1N sodium hydroxide solution (50 cc.). The organic layer is decanted, washed with water (2 × 50 cc.), dried over anhydrous sodium sulphate in the presence of decolourising charcoal, filtered and then evaporated to dryness under reduced pressure. The residue is recrystallised from acetonitrile (95 cc.) and the product obtained is heated for 10 minutes with ethanol (65 cc.) at the reflux temperature. The insoluble product is then isolated from the boiling solution by filtration, after which it is washed with boiling ethanol (2 × 10 cc.). After drying, 6-(7-chloro-1,8-naphthyridin-2-yl)-5-cyclohexylaminocarbonyloxy-7-oxo-6,7-dihydro-5H-pyrrolo[3,4-b]pyrazine (1.8 g.), melting at 264° C., is obtained.

EXAMPLE 40 n-Butyl isocyanate (2 g.) is added to a suspension of 6-(7-chloro-1,8-naphthyridin-2-yl)-5-hydroxy-7-oxo-2,3,6,7-tetrahydro-5H-1,4-oxathiino[2,3-c]pyrrole (3.36 g.) in acetonitrile (67 cc.). The reaction mixture is heated to a temperature of about 80° C. for 6 hours. After cooling, the insoluble product is filtered off and washed with acetonitrile (2 × 10 cc.). After recrystallisation from acetonitrile (60 cc.), 6-(7-chloro-1,8-naphthyridin-2-yl)-5-n-butylaminocarbonyloxy-7-oxo-2,3,6,7-tetrahydro-5H-1,4-oxathiino[2,3-c]pyrrole (3.1 g.), melting at 262° C., is obtained.

6-(7-Chloro-1,8-naphthyridin-2-yl)-5-hydroxy-7-oxo-2,3,6,7-tetrahydro-5H-1,4-oxathiino[2,3-c]pyrrole can be prepared by reaction of potassium borohydride (0.54 g.) with 6-(7-chloro-1,8-naphthyridin-2-yl)-5,7-dioxo-2,3,6,7-tetrahydro-5H-1,4-oxathiino[2,3-c]pyrrole (3.59 g.) in methanol (30 cc.) at a temperature of about 30° C. This gives 6-(7-chloro-1,8-naphthyridin-2-yl)-5-hydroxy-7-oxo-2,3,6,7-tetrahydro-5H-1,4-oxathiino[2,3-c]pyrrole (3.06 g.) melting at 277° C.

6-(7-Chloro-1,8-naphthyridin-2-yl)-5,7-dioxo-2,3,6,7-tetrahydro-5H-1,4-oxathiino[2,3-c]pyrrole can be prepared by heating a solution of the anhydride of 5,6-dihydro-1,4-oxathiine-2,3-dicarboxylic acid (3.44 g.) with N-hydroxysuccinimide (2.86 g.) in anhydrous dimethylformamide (100 cc.) at a temperature of about 60° C. After 18 hours heating, 2-amino-7-chloro-1,8-naphthyrid (3.6 g.) and N,N-dicyclohexylcarbodiimide (8 g.) are added to the reaction mixture. The mixture is then heated at temperature of about 75° C. for 24 hours. After cooling water (1 cc.) is added to the reaction mixture and the insoluble product is filtered off, after which it is washed with methylene chloride (200 cc.). After drying 6-(7-chloro-1,8-naphthyridin-2-yl)-5,7-dioxo-2,3,6,7-tetrahydro-5H-1,4-oxathiino[2,3-c]pyrrole (4.4 g.), melting at 264° C., is obtained.

The anhydride of 5,6-dihydro-1,4-oxathiine-2, dicarboxylic acid can be prepared in accordance with the method described by P. ten Haken, J. Het. Chem., 7, 121 (1970).

The present invention includes within its scope pharmaceutical compositions which comprise, as active ingredient, at least one of the heterocyclic compounds of general formula I or — when appropriate — non-toxic acid addition salt thereof, in association with a pharmaceutical carrier or coating. The invention includes especially such preparations made up for oral parenteral or rectal administration, or as ointments.

Solid compositions for oral administration include tablets, pills, powders and granules. In such solid compositions the active compound is admixed with at least one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water or liquid paraffin. Besides inert diluents such compositions may also comprise adjuvants, such as wetting, emulsifying and suspending agents, and sweetening, flavouring and aromatizing agents. The compositions according to the invention, for oral administration, also include capsules of absorbable material such as gelatin containing the active substance with or without the addition of diluents or excipients.

Compositions according to the invention for parenteral administration include sterile aqueous or non-aqueous solutions, suspensions or emulsions. Examples of non-aqueous solvents or vehicles are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilized by, for example, filtration through a bacteria-retaining filter, by incorporation in the compositions of sterilizing agents, by irradiation, or by heating. They may also be manufactured in the form of sterile solid compositions, which can be dissolved in sterile water or some other sterile injectable medium immediately before use.

Compositions for rectal administration are suppositories which contain, in addition to the active substance, excipients such as cacao butter or a suitable wax base.

In human therapy the compositions can be used, in particular, as tranquilisers, hypnotics, anti-epileptic agents and anti-spasmodics.

The percentage of active ingredient in the compositions of the invention may be varied, it being necessary that it should constitute a proportion such that a suitable dosage shall be obtained. The dosage depends on the desired therapeutic effect, on the route of administration and on the duration of the treatment. In human therapy the compositions when administered orally to an adult should generally give doses between 5 mg. and 100 mg. of active substance per day. In general the physician will decide the posology considered appropriate, taking into account the age and weight and other factors intrinsic to the patient being treated.

The following Examples illustrate pharmaceutical compositions according to the invention.

EXAMPLE 41

Tablets containing 25 mg. of active compound and having the following composition are prepared in accordance with the usual technique:

| | |
|---|---|
| 2-(7-chloro-1,8-naphthyridin-2-yl)-3-n-butylaminocarbonyloxy-isoindolin-1-one | 0.025 g. |
| starch | 0.090 g. |
| precipitated silica | 0.030 g. |
| magnesium stearate | 0.005 g. |

EXAMPLE 42

Tablets containing 25 mg. of active compound and having the following composition are prepared in accordance with the usual technique:

| | |
|---|---|
| 2-(7-chloro-1,8-naphthyridin-2-yl)-3-cyclopentylcarbamoyloxy-isoindolin-1-one | 0.025 g. |
| starch | 0.090 g. |
| precipitated silica | 0.030 g. |
| magnesium stearate | 0.005 g. |

EXAMPLE 43

Tablets containing 25 mg. of active compound and having the following composition are prepared in accordance with the usual technique:

| | |
|---|---|
| 5-n-butylaminocarbonyloxy-6-(7-chloro-1,8-naphthyridin-2-yl)-7-oxo-6,7-dihydro-5H-pyrrolo[3,4-b]pyrazine | 0.025 g. |
| starch | 0.090 g. |
| precipitated silica | 0.030 g. |
| magnesium stearate | 0.005 g. |

We claim:

1. A heterocyclic compound of the formula:

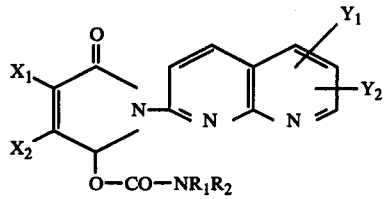

wherein the pyrroline ring and the symbols $X_1$ and $X_2$ together form an isoindoline nucleus or an isoindoline nucleus substituted by one or two atoms or radicals selected from halogen, alkyl of 1 through 4 carbon atoms, alkoxy of 1 through 4 carbon atoms, nitro and trifluoromethyl, the symbols $Y_1$ and $Y_2$ each represent hydrogen, halogen, alkyl of 1 through 4 carbon atoms, alkoxy of 1 through 4 carbon atoms, or cyano, and the symbols $R_1$ and $R_2$ together with the nitrogen atom to which they are attached form a morpholino ring, and when appropriate non-toxic pharmaceutically acceptable acid addition salts thereof.

2. A heterocyclic compound according to claim 1 wherein the pyrroline ring and the symbols $X_1$ and $X_2$ together form an isoindoline nucleus or an isoindoline nucleus substituted by halogen or trifluoromethyl, $Y_1$ represents halogen in the 7-position of the 1,8-naphthyridin-2-yl nucleus, $Y_2$ represents hydrogen, and $R_1$ and $R_2$ together with the nitrogen atom to which they are attached form a morpholino ring.

3. A heterocyclic compound according to claim 1 wherein the pyrroline ring and the symbols $X_1$ and $X_2$ form an isoindoline nucleus, $Y_1$ represents chlorine in the 7-position of the 1,8-naphthyridin-2-yl nucleus, $Y_2$ represents hydrogen atom, and $R_1$ and $R_2$ together with the nitrogen atom to which they are attached form a morpholino ring.

4. A heterocyclic compound according to claim 1 wherein halogen is chlorine.

5. A heterocyclic compound according to claim 1 which is 2-(7-chloro-1,8-naphthyridin-2-yl)-3-[(4-morpholino)carbonyloxy]-isoindolin-1-one.

6. Tranquilliser, hypnotic, anti-convulsant and anti-spasmodic pharmaceutical compositions which comprise, as an active ingredient, an effective amount of a heterocyclic compound as claimed in claim 1, or — when appropriate — a non-toxic pharmaceutically acceptable acid addition salt thereof, in association with a significant amount of a pharmaceutical carrier.

* * * * *